US011112367B2

(12) United States Patent
Wang et al.

(10) Patent No.: US 11,112,367 B2
(45) Date of Patent: Sep. 7, 2021

(54) DEVICE AND METHOD FOR ANALYZING TOTAL CYANIDE IN WATER SAMPLES

(71) Applicant: FUJIAN KELUNGDE ENV. TECH. CO., LTD, Fujian (CN)

(72) Inventors: Shuiji Wang, Fujian (CN); Jianping Cui, Fujian (CN); Zhuobin Weng, Fujian (CN)

(73) Assignee: FUJIAN KELUNGDE ENV. TECH. CO., LTD, Zhangzhou (CN)

( * ) Notice: Subject to any disclaimer, the term of this patent is extended or adjusted under 35 U.S.C. 154(b) by 186 days.

(21) Appl. No.: 16/574,534

(22) Filed: Sep. 18, 2019

(65) Prior Publication Data

US 2020/0011805 A1    Jan. 9, 2020

Related U.S. Application Data

(63) Continuation of application No. PCT/CN2018/078819, filed on Mar. 13, 2018.

(30) Foreign Application Priority Data

Jul. 20, 2017  (CN) ............................ 20171059345.8

(51) Int. Cl.
| | | |
|---|---|---|
| *G01N 21/78* | (2006.01) | |
| *B01L 3/00* | (2006.01) | |
| *G01N 31/22* | (2006.01) | |
| *G01N 33/18* | (2006.01) | |

(52) U.S. Cl.
CPC .............. *G01N 21/78* (2013.01); *B01L 3/502* (2013.01); *B01L 3/5082* (2013.01); *G01N 31/22* (2013.01); *G01N 33/18* (2013.01); *B01L 2300/0663* (2013.01); *B01L 2400/0622* (2013.01)

(58) Field of Classification Search
CPC ........ G01N 21/78; G01N 31/22; G01N 33/18; B01L 3/502; B01L 3/5082; B01L 2300/0663; B01L 2400/0622
See application file for complete search history.

(56) References Cited

U.S. PATENT DOCUMENTS

2013/0045151 A1    2/2013    Kim et al.

FOREIGN PATENT DOCUMENTS

| CN | 102495013 A | 6/2012 |
|---|---|---|
| CN | 202421060 U | 9/2012 |
| CN | 203965314 U | 11/2014 |
| CN | 104977265 A | 10/2015 |
| CN | 107367475 A | 11/2017 |

*Primary Examiner* — Jennifer Wecker
*Assistant Examiner* — Kathryn Elizabeth Limbaugh

(57) ABSTRACT

A device and a method of analyzing total cyanide in water samples, including a mixing tube, a stripping tube, a sampling pipe, a reaction pipe, a peristaltic pump, an air pump, a UV digester, a heater, a condenser, a drain pipe and a water sample detector. The mixing tube, the stripping tube, the sampling pipe and the reaction pipe are respectively connected to the peristaltic pump. The mixing tube is connected to the reaction pipe. A bottom of the stripping tube, the air pump, the UV digester, the heater and the condenser and are sequentially connected. The condenser is connected to the mixing tube. An upper portion of the stripping tube, the sampling pipe and the reaction pipe are connected to the drain pipe. An absorbance of the water in the mixing tube is measured by the sample detector, and used to calculate the total cyanide content by spectrophotometry.

10 Claims, 2 Drawing Sheets

DEVICE AND METHOD FOR ANALYZING TOTAL CYANIDE IN WATER SAMPLES

CROSS-REFERENCE TO RELATED APPLICATIONS

This application is a continuation of International Patent Application No. PCT/CN2018/078819, filed on Mar. 13, 2018, which claims the benefit of priority from Chinese Patent Application No. 201710593454.8, filed on Jul. 20, 2017. The contents of the aforementioned application, including any intervening amendments thereto, are incorporated herein by reference in its entirety.

TECHNICAL FIELD

The invention relates to water quality analysis, and more particularly to a device and a method for analyzing total cyanide in water samples.

BACKGROUND OF THE INVENTION

Cyanide is violent in toxicity. However, it can be widely found in nature due to its wide industrial application. Environmental cyanide pollutants are mainly derived from the sewage discharged from the chemical, mining, coking and fertilizer production fields.

Spectrophotometry is generally applied to the analysis of cyanide due to the characteristics of simple operation, high accuracy and sensitivity, available conditions, low detection limit and good reproducibility. However, the relatively complicated operation process limits the application.

The existing devices for analyzing total cyanide fail to meet the requirements of simple and high-efficiency determination due to the complicated structure, large size and low automation level. Thus, there is an urgent need to further optimize the existing analysis devices.

SUMMARY OF THE INVENTION

The invention aims to provide a device and a method for analyzing total cyanide in water samples to enable the real-time and online monitoring of water quality, improving the automation level in water analysis.

The above object is achieved by the following technical solutions.

This application provides a device for analyzing total cyanide in a water sample, comprising: a mixing tube, a stripping tube, a sampling pipe, a reaction pipe, a peristaltic pump, an air pump, a UV digester, a heater, a condenser, a drain pipe, and a water sample detector;

wherein the mixing tube, the stripping tube, the sampling pipe, and the reaction pipe are respectively connected to the peristaltic pump; the mixing tube is connected to the reaction pipe; a bottom of the stripping tube, the air pump, the UV digester, the heater and the condenser are sequentially connected; the condenser is connected to the mixing tube; an upper portion of the stripping tube, the sampling pipe and the reaction pipe are respectively connected to the drain pipe; and the water sample detector is able to detect and analyze parameters of the water sample in the mixing tube.

In which, the reaction pipe and the sampling pipe each comprise a plurality of three-way valves, and respective three-way valves comprise a normally closed end, a common end and a normally open end.

In which, the reaction pipe comprises three-way valves Q0, Q1, Q2, Q3, Q4 and Q5;

wherein a normally closed end of Q0 is connected to a pure water pipe; a common end of Q0 is connected to a normally closed end of Q1; a common end of Q1 is connected to a normally open end of Q3; a normally open end of Q1 is connected to a normally open end of Q2; a normally closed end of Q2 is connected to the drain pipe; a common end of Q2 is connected to the mixing tube; normally closed ends of Q3, Q4 and Q5 are respectively connected to chemical agent tubes R1, R2 and R3; a common end of Q3 is connected to a normally open end of Q4; a common end of Q4 is connected to a normally open end of Q5; and a common end of Q5 is connected to the peristaltic pump.

In which, the sampling pipe comprises the three-way valves Q6, Q7, Q8, Q9 and Q10;

wherein normally closed ends of Q6, Q7, Q8, Q9 and Q10 are respectively connected to the pure water pipe, a water sample-monitoring tube, a standard sample tube, the drain pipe and a chemical agent tube R4; a normally open end of Q6 is connected to an air inlet pipe; common ends of Q6, Q7, Q8 and Q9 are respectively connected to normally open ends of Q7, Q8, Q9 and Q10; and a common end of Q10 is connected to the peristaltic pump.

Further, the peristaltic pump is provided with two connecting ports, which are respectively connected to common ends of two simultaneously-operated three-way valves QA1 and QA2; normally open ends of QA1 and QA2 are respectively connected to the reaction pipe and the mixing tube; and normally closed ends of QA1 and QA2 are respectively connected to the sampling pipe and the stripping tube.

The mixing tube is connected to the condenser through three-way valves QB and QC; and the air pump is connected to the bottom of the stripping tube through a three-way valve QD.

The invention also discloses a method for analyzing total cyanide in a water sample, using the device for analyzing total cyanide in a water sample, and the method comprises the following steps.

(1) Emptying a stripping tube and a mixing tube in a thermostatic water bath; and performing a heating process to obtain a constant temperature inside the heater;

(2) pumping pure water into the mixing tube followed by a standing to obtain an initial absorbance of the water sample;

(3) pumping chemical agents R1 and R2, as well as a small amount of pure water from the reaction pipe to the mixing tube through a peristaltic pump to produce a mixed chemical agent solution; wherein R1 is a mixed solution of a 18-22 g/L potassium hydrogen phthalate solution and a 2-4 g/L sodium hydroxide solution, and R2 is a 3-5 g/L chloramine T solution;

(4) pumping a sample to be detected from a sampling pipe to the stripping tube through the peristaltic pump;

(5) adding a chemical agent R4 into the stripping tube for catalytic removal; wherein R4 is a mixed solution of a 3-5 g/L sodium hydroxide solution and a 18-22 g/L citric acid solution;

(6) pumping the sample to be detected in the stripping tube by an air pump to a UV digester and then to the heater; instantaneously vaporizing the sample to be detected by distillation in the heater to release a cyanide gas; cooling the cyanide gas into a cyanide liquid by a condenser; allowing the cyanide liquid to flow into the mixing tube to react with the mixed chemical agent solution obtained in step (3); and repeating the distillation until the sample is completely vaporized;

(7) adding a chemical agent R3 to the mixing tube for color development, wherein R3 is a mixed solution of pyridine with a volume fraction of 99% or more, barbituric acid with a mass concentration of 28-32 g/L and concentrated hydrochloric acid; subjecting the reaction mixture to standing for a certain period after the color development; measuring a final absorbance of the reaction mixture; and calculating the total cyanide content in the sample to be detected according to spectrophotometry; and (8) pumping pure water to empty and clean the mixing tube, the stripping tube, the UV digester, the heater and the condenser.

Wherein the sample to be detected in step (4) is a water sample to be monitored or a standard sample; the water sample to be monitored is collected to the sampling pipe through a water sample-monitoring tube, and then pumped into the stripping tube through the peristaltic pump; and the standard sample is collected to the sampling pipe through a standard sample tube, and then pumped into the stripping tube through the peristaltic pump.

In some embodiments, in step (3), air is pumped into the mixing tube to completely mix the chemical agents R3 and R4 with pure water; and in step (4), the excess sample to be detected in the stripping tube is discharged from a drain pipe which is provided at an upper portion of the stripping tube.

In some embodiments, in step (1), the heater has an internal temperature of 80° C., a pulse-heating temperature of 162° C., and a maximum temperature of 165° C.

The invention has the following beneficial effects.

The device provided herein for analyzing total cyanide in a water sample has a reasonable structure, high automatization level, and rapid and efficient analysis, realizing real-time and online monitoring of water quality.

Figure 1:
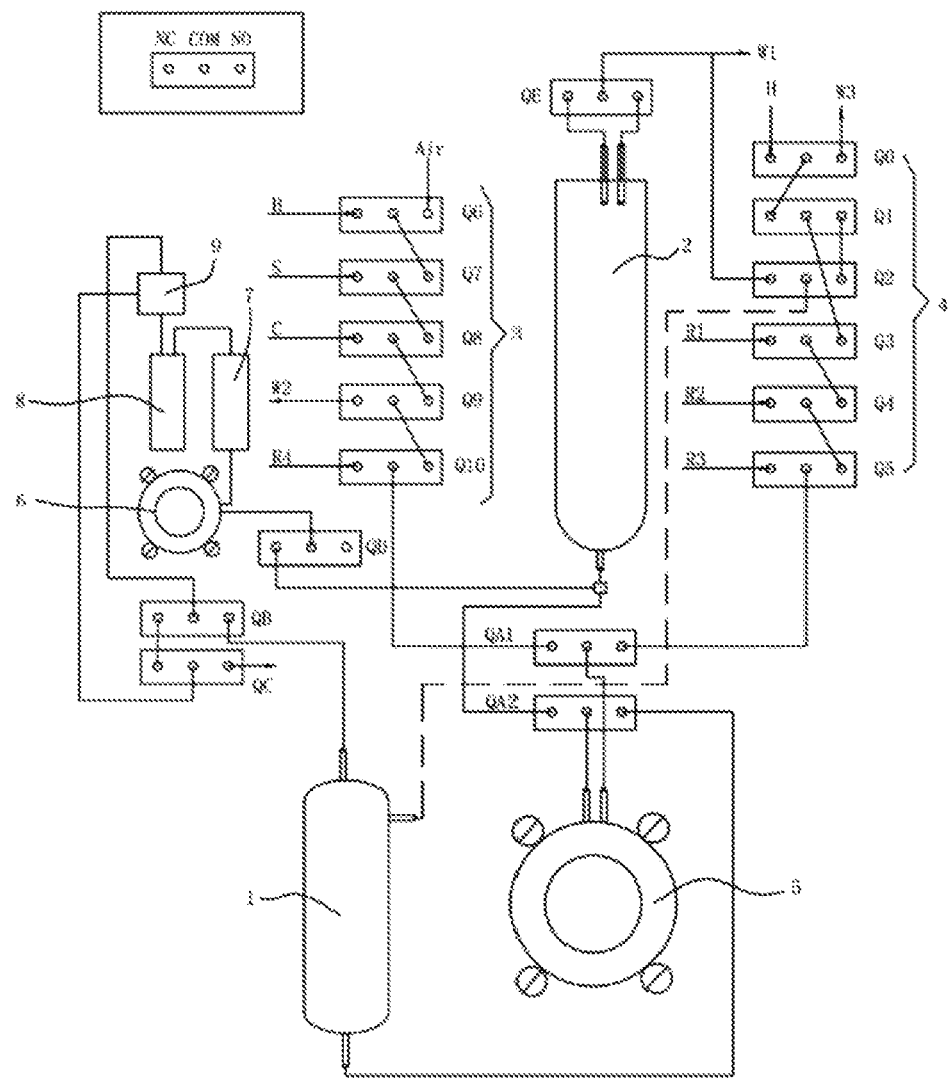
FIG. 1 schematically shows a device for analyzing total cyanide in water samples of the invention.

In the drawings, 1-mixing tube; 2-stripping tube; 3-sampling pipe; 4-reaction pipe; 5-peristaltic pump; 6-air pump; 7-UV digester; 8-heater; 9-condenser; and 10-drain pipe.

DETAILED DESCRIPTION OF EMBODIMENTS

The invention will be further described in detail below with reference to the drawings and embodiments to make the objects, technical solutions and advantages of the invention clear.

Figure 2:
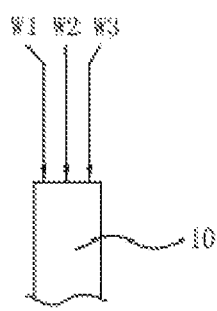
FIG. 2 schematically shows the connection of a drain pipe of the invention.

The invention discloses a device of analyzing total cyanide in a water sample. As shown in FIGS. 1 and 2, the device includes a mixing tube 1, a stripping tube 2, a sampling pipe 3, a reaction pipe 4, a peristaltic pump 5, an air pump 6, a UV digester 7, a heater 8, a condenser 9, a drain pipe 10 and a water sample detector (not shown in the figures).

The mixing tube 1, the stripping tube 2, the sampling pipe 3, and the reaction pipe 4 are respectively connected to the peristaltic pump 5. The mixing tube 1 is connected to the reaction pipe 4. A bottom of the stripping tube 2, the air pump 6, the UV digester 7, the heater 8, and the condenser 9 are sequentially connected. An upper portion of the stripping tube 2, the sampling pipe 3, and the reaction pipe 4 are respectively connected to the drain pipe 10. The water sample detector is able to detect and analyze parameters of the water sample in the mixing tube 1.

The pipes of the device of the invention include a plurality of three-way valves, and respective three-way valves include a normally closed end (NC end), a common end (COM end) and a normally open end (NO end). When the three-way valve is free of power (i.e., out of operation), the COM are communicated with the NO end while are not communicated with the NC end. When the three-way valve is energized (i.e., under operation), the COM end are communicated with the NC end while are not communicated with the NO end.

The peristaltic pump 5 is provided with two connection ports, which are respectively connected to the common ends of two simultaneously-operated three-way valves QA1 and QA2. The two normally open ends of the three-way valves QA1 and QA2 are respectively connected to the reaction pipe 4 and the mixing tube 1, and the two normally closed ends of the three-way valves QA1 and QA2 are respectively connected to the sampling pipe 3 and the stripping tube 2. The mixing tube 1 is connected to the condenser 9 sequentially through three-way valves QB and QC. The air pump 6 is connected to the bottom of the stripping tube 2 through a three-way valve QD.

The reaction pipe 4 includes three-way valves Q0, Q1, Q2, Q3, Q4 and Q5, where a normally closed end of Q0 is connected to a pure water pipe; a common end of Q0 is connected to a normally closed end of Q1; a common end of Q1 is connected to a normally open end of Q3; a normally open end of Q1 is connected to a normally open end of Q2; a normally closed end of Q2 is connected to the drain pipe; a common end of Q2 is connected to the mixing tube 1; normally closed ends of Q3, Q4 and Q5 are respectively connected to chemical agent tubes R1, R2 and R3; a common end of Q3 is connected to a normally open end of Q4; a common end of Q4 is connected to a normally open end of Q5; and a common end of Q5 is connected to the peristaltic pump 5.

The sampling pipe 3 includes three-way valves Q6, Q7, Q8, Q9 and Q10, where the normally closed ends of Q6, Q7, Q8, Q9 and Q10 are respectively connected to the pure water tube 11, a water sample-monitoring tube S, a standard sample tube C, the drain pipe 10 (tubes W1, W2, W3 all are connected to the drain pipe) and a chemical agent tube R4. A normally open end of Q6 is connected with an air inlet pipe. Common ends of Q6, Q7, Q8 and Q9 are respectively connected to normally open ends of Q7, Q8, Q9 and Q10. A common end of Q10 is connected to the peristaltic pump 5.

The application also discloses a method for analyzing total cyanide in a water sample using the above device, and the steps are specifically described below.

Step (1)

A stripping tube 2 and a mixing tube 1 were emptied in a thermostatic water bath. Then a heating process was performed to obtain a constant temperature inside a heater.

After the device was started, the stripping tube 2 and the mixing tube 1 were firstly emptied. Two three-way valves QA1 and QA2 connected to the peristaltic pump 5 and the three-way valve Q9 were operated, and the peristaltic pump 5 was operated to rotate counterclockwise to empty the liquid in the stripping tube 2 through the pipe W2. When the stripping tube 2 was completely emptied, the corresponding valves and the peristaltic pump 5 were closed. Then the valve Q1 was opened, and the peristaltic pump 5 was operated to rotate counterclockwise to empty the liquid in the mixing tube 1 through the pipe W3. After that, the valve Q1 and the peristaltic pump 5 were closed. The heating was performed as soon as the device was started, so that the heater 8 had an internal temperature of 80° C., a pulse-heating temperature of 162° C. and a maximum temperature of 165° C.

Step (2) Detection of Pure Water

Pure water was pumped into the mixing tube followed by a standing and measured for an initial absorbance (i.e., abs-s).

Valves Q0, Q1 and QB were operated, and the peristaltic pump 5 was regulated to clockwise rotate, so that the pure water was pumped from the pipe H into the mixing tube 1. After the mixing tube was filled with pure water, all valves were closed, and the peristaltic pump 5 was operated to rotate clockwise for mixing and then rotate counterclockwise for a while followed by a standing to measure abs-s.

Step (3) Feeding of Chemical Agents to the Mixing Tube

Chemical agents R1 and R2, as well as a small amount of pure water were pumped from the reaction pipe 4 to the mixing tube lusing the peristaltic pump 5 to produce a mixed chemical agent solution, where R1 was a mixed solution of a 18-22 g/L potassium hydrogen phthalate solution and a 2-4 g/L sodium hydroxide solution, and R2 was a 3-5 g/L chloramine T solution. Air was pumped into the mixing tube to completely mix the chemical agents R3 and R4 with pure water.

(1) Valve Q3 was opened, and the peristaltic pump 5 was operated to rotate slowly for a certain period to pump the chemical agent R1. After the chemical agent R1 was completely fed, the peristaltic pump 5 and Q3 were closed.

(2) Valve Q4 was opened, and the peristaltic pump 5 was operated to rotate slowly for a certain period to pump the chemical agent R2. After the chemical agent R2 was completely fed, the peristaltic pump 5 and Q4 were closed.

(3) Valves Q0 and Q1 were opened, and the peristaltic pump 5 was operated to rotate slowly for a certain period to pump the pure water from the H tube. After the pure water was completely fed, the peristaltic pump 5, Q0 and Q1 were closed. Then the peristaltic pump 5 was operated to rotate clockwise to mix and gather all the liquids in the mixing tube 1. After that, the peristaltic pump 5 was stopped.

Step (4) Analysis

A sample to be detected was pumped from the sampling pipe 3 to the stripping tube 2 using the peristaltic pump 5. The excess sample in the stripping tube 2 was discharged from a drain pipe which was provided at an upper portion of the stripping tube 2.

The sample to be detected was a standard sample or a water sample. Generally, the device needed to be calibrated with the standard sample after a period of operation, for example, the device can be calibrated once a month. The standard sample was collected to the sampling pipe 3 through a standard sample tube C, and then pumped into the stripping tube 2 through the peristaltic pump 5. When analyzed online for total cyanide, the water sample to be monitored was collected to the sampling pipe 3 through a water sample-monitoring tube S and pumped into the stripping tube 2 through the peristaltic pump 5. In this step, the valves were operated as follows.

When the standard sample was introduced, valves Q8, QA1 and QA2 were opened, and the peristaltic pump 5 was regulated to rotate clockwise to pump the standard sample from pipe C to the stripping tube 2. The excess liquid in the stripping tube 2 was discharged through a normally open end of QE and the waste liquid pipe W1. After the stripping tube 2 was added with enough sample, valve Q8 was closed, and the peristaltic pump 5 was regulated to continuously rotate clockwise, so that the air from the air inlet pipe at a normally open end of Q6 was pumped to push all the sample in the sampling pipe 3 to the stripping tube 2 and facilitate the mixing. After the above process, the valves and the peristaltic pump 5 were closed.

When the water sample to be monitored was introduced, valves Q7 and QA were opened, and the peristaltic pump 5 was regulated to rotate clockwise to pump the water sample from a pipe 5 to the stripping tube 2. The excess liquid in the stripping tube 2 was discharged through a normally open end of QE and the waste liquid pipe W1. After the stripping tube 2 was added with enough sample, the valve Q7 was closed, while the peristaltic pump 5 continued rotating clockwise, so that the air from the air inlet pipe at the normally open end of Q6 was pumped to push all the sample in the sampling pipe 3 to the stripping tube 2 and facilitate the mixing. After the above process, the valves Q7, QA, QE, Q6 and the peristaltic pump 5 were closed.

Step (5) Feeding of the Agent to the Stripping Tube

A chemical agent R4 was added into the stripping tube 2 for catalytic elimination, where R4 was a mixed solution of a 3-5 g/L sodium hydroxide solution and a 18-22 g/L citric acid solution. The chemical agent R4 was used for catalytic elimination instead of color development.

Valves QA, Q10 and QE were opened, and the peristaltic pump 5 was regulated to rotate slowly to pump the chemical agent R4 to the stripping tube 2. After the stripping tube 2 was added with enough sample, the valve Q10 was closed, while the peristaltic pump 5 continued rotating, so that the air from the air inlet pipe at the normally open end of Q6 was pumped to push all the sample in the sampling pipe 3 to the stripping tube 2 to facilitate the mixing. After the above process, the valves QA, Q10, QE, Q6 and the peristaltic pump 5 were closed.

Step (6) Distillation

The sample to be detected in the stripping tube 2 was pumped by the air pump 6 to the UV digester and then to the heater 8. The sample to be detected was instantaneously vaporized in the heater by distillation to release a cyanide gas. The cyanide gas was cooled by a condenser 9 and flowed into the mixing tube 1 to react with the mixed chemical agent solution obtained in step (3). The distillation was repeated until the sample to be detected was completely vaporized.

During the distillation, the condenser 9, the UV digester 7 and the air pump 6 were always turned on, and the valve QD was also opened. A certain amount of water sample in the stripping tube 2 was pumped into the air pump 6, and then the valve QD was closed, so that The air pump 6 pumped air to quickly push the water sample to the UV digester 7, and then to the heater 8. The water sample was instantaneously vaporized by heating to release the cyanide gas. The cyanide gas was condensed by a condenser 9 and flowed into the mixing tube 1. The heater 8 was added with a little amount of water sample each time, since the instantaneous vaporization was required for the violent reaction. The distillation was repeated until the sample was completely vaporized. After the vaporized sample was collected for a while, the peristaltic pump 5 was operated to rotate counterclockwise to mix the liquid in the mixing tube 1 for reaction.

Step (7) Color Development

A chemical agent R3 was added to the mixing tube 1 for color development, where R3 was a mixed solution of pyridine with a volume fraction of 99% or more, barbituric acid with a mass concentration of 28-32 g/L and concentrated hydrochloric acid (with a mass fraction of 20% or more). The reaction mixture was subjected to standing for a certain period after the color development, and then measured for a final absorbance (i.e., abs-e). The total cyanide content in the sample to be detected was calculated according to the spectrophotometry.

The valves Q5 and QB were opened, and the peristaltic pump 5 was regulated to rotate slowly to pump the chemical agent R3 to the mixing tube 1. Then the Q5 was closed, and the peristaltic pump 5 was regulated to rotate counterclockwise to facilitate the mixing. After the color development, the reaction mixture was subjected to standing for a while and measured for the abs-e.

Step (8) Cleaning

Pure water was pumped to empty and clean the mixing tube 1, the stripping tube 2, the UV digester 7, the heater 8 and the condenser 9.

In the washing process, the entire pipes were emptied by introducing the pure water from the H tube and then washed with the pure water or 5 wt % sulfuric acid. The entire reaction process was finished until the pipes were completely washed.

The standard sample in this example was a 50 mg/L cyanide standard solution for water analysis, which was serially diluted with 0.01 mol/L sodium hydroxide to prepare a series of standard solutions respectively with a concentration of 0.000, 0.100, 0.400 and 0.500 mg/L. The chemical agents used herein were shown in Table 1.

TABLE 1

Compositions of chemical agents

| Label | Components | Example 1 | Example 2 | Example 3 |
|---|---|---|---|---|
| R1 | Potassium hydrogen phthalate ($C_8H_5KO_4$) | 20.5 g/L | 18 g/L | 22 g/L |
|  | Sodium Hydroxide (NaOH) | 2.3 g/L | 2 g/L | 4 g/L |
| R2 | Chloramine-T ($C_7H_7ClNNaO_2S \cdot 3H_2O$) | 4 g/L | 5 g/L | 3 g/L |
| R3 | Barbituric acid ($C_4N_4N_2O_3$) | 30 g/L | 32 g/L | 28 g/L |
|  | Pyridine ($C_5H_5N$) | 99.5 g/L | 99.7 g/L | 99.4 g/L |
|  | Hydrochloric acid (HCl) | 36% | 36% | 37% |
| R4 | Sodium hydroxide (NaOH) | 4 g/L | 3 g/L | 5 g/L |
|  | Citric Acid ($C_6H_8O_7 \cdot H_2O$) | 20 g/L | 18 g/L | 22 g/L |

A surface water sample, a groundwater sample, an electroplating wastewater sample and a coking wastewater sample from a steel plant were used as samples to be analyzed with the chemical agents in Example 1 using the device and the method of the invention. The results were shown in Tables 2-4.

TABLE 2

Test results of standard samples

| Standard solution (mg/L) | Absorbance (peak height) | Total cyanide concentration (mg/L) |
|---|---|---|
| 0.000 | 0.1168 | 0.002 |
| 0.100 | 0.3025 | 0.110 |
| 0.400 | 0.7759 | 0.400 |
| 0.500 | 0.9376 | 0.498 |

Working curve: Y = 1.6248x + 0.127 $R^2$ = 0.9994

TABLE 3

Test results of water samples

| Sample ID | Sample concentration | Spiking amount | Spiked concentration | Recovery rate |
|---|---|---|---|---|
| Surface water | 0.000 | 0.200 | 0.196 | 98% |
| Groundwater | 0.001 | 0.200 | 0.202 | 101.2% |
| Electroplating wastewater | 0.356 | 0.200 | 0.554 | 99.1% |
| Coking wastewater from a steel plant | 0.285 | 0.200 | 0.480 | 97.5% |

TABLE 4

Analysis of precision in determining total cyanide content in a standard sample (0.400 mg/L) with chemical agents

| Number | Absorbance (peak height) | Total cyanide concentration (mg/L) |
|---|---|---|
| 1 | 0.7748 | 0.399 |
| 2 | 0.7795 | 0.402 |
| 3 | 0.7759 | 0.400 |
| 4 | 0.7818 | 0.403 |
| 5 | 0.7780 | 0.401 |
| 6 | 0.7813 | 0.403 |
| 7 | 0.7730 | 0.398 |

RSD = 0.487%

The invention had a linear range of 0.02-0.5 mg/L, a linear correlation coefficient of r≥0.994, a detection limit of 0.001 mg/L and a spiked recovery rate of 95-105%. Moreover, the invention also showed a relative standard deviation of 0.487% for the 0.4 mg/L standard sample, allowing for high precision.

To sum up, the device of the application has a reasonable structure, can realize fully automated control of total cyanide of water samples, and is suitable for a wide range of applications.

Described above are merely preferred embodiments of the invention, which are not intended to limit the scope of the invention. Any changes or replacements made by those skilled in the art without departing from the spirit of the disclosure should fall within the scope of the invention.

INDUSTRIAL APPLICABILITY

The application can be applied to the analysis and monitoring of total cyanide in various water samples such as drinking water, surface water, domestic and industrial sewage to realize remote real-time online monitoring of the discharged wastewater.

What is claimed is:

1. A device for analyzing total cyanide in a water sample, comprising: a mixing tube, a stripping tube, a sampling pipe, a reaction pipe, a peristaltic pump, an air pump, a UV digester, a heater, a condenser, a drain pipe and a water sample detector;

wherein the mixing tube, the stripping tube, the sampling pipe and the reaction pipe are respectively connected to the peristaltic pump; the mixing tube is connected to the reaction pipe; a bottom of the stripping tube, the air pump, the UV digester, the heater and the condenser are sequentially connected; the condenser is connected to the mixing tube; an upper portion of the stripping tube, the sampling pipe and the reaction pipe are respectively connected to the drain pipe; and the water sample detector is able to detect and analyze parameters of the water sample in the mixing tube.

2. The device of claim 1, wherein the reaction pipe and the sampling pipe each comprise a plurality of three-way valves, and respective three-way valves comprise a normally closed end, a common end and a normally open end.

3. The device of claim 2, wherein the reaction pipe comprises three-way valves Q0, Q1, Q2, Q3, Q4 and Q5; wherein a normally closed end of Q0 is connected to a pure water pipe; a common end of Q0 is connected to a normally closed end of Q1; a common end of Q1 is connected to a normally open end of Q3; a normally open end of Q1 is connected to a normally open end of Q2; a normally closed end of Q2 is connected to the drain pipe; a common end of Q2 is connected to the mixing tube; normally closed ends of Q3, Q4 and Q5 are respectively connected to chemical agent tubes R1, R2 and R3; a common end of Q3 is connected to a normally open end of Q4; a common end of Q4 is connected to a normally open end of Q5; and a common end of Q5 is connected to the peristaltic pump.

4. The device of claim 2, wherein the sampling pipe comprises three-way valves Q6, Q7, Q8, Q9 and Q10; wherein normally closed ends of Q6, Q7, Q8, Q9 and Q10 are respectively connected to a pure water pipe, a water sample-monitoring tube, a standard sample tube, the drain pipe and a chemical agent tube R4; a normally open end of Q6 is connected to an air inlet pipe; common ends of Q6, Q7, Q8 and Q9 are respectively connected to normally open ends of Q7, Q8, Q9 and Q10; and a common end of Q10 is connected to the peristaltic pump.

5. The device of claim 1, wherein the peristaltic pump is provided with two connecting ports, which are respectively connected to common ends of two simultaneously-operated three-way valves QA1 and QA2; normally open ends of QA1 and QA2 are respectively connected to the reaction pipe and the mixing tube; and normally closed ends of QA1 and QA2 are respectively connected to the sampling pipe and the stripping tube.

6. The device of claim 1, wherein the mixing tube is connected to the condenser through three-way valves QB and QC; and the air pump is connected to the bottom of the stripping tube through a three-way valve QD.

7. A method for analyzing total cyanide in a water sample using the device of claim 1, comprising:
   (1) emptying a stripping tube and a mixing tube in a thermostatic water bath; and performing a heating process to obtain a constant temperature inside a heater;
   (2) pumping pure water into the mixing tube followed by a standing to obtain an initial absorbance of the water sample;
   (3) pumping chemical agents R1 and R2, as well as a small amount of pure water from a reaction pipe to the mixing tube through a peristaltic pump to produce a mixed chemical agent solution; wherein R1 is a mixed solution of a 18-22 g/L potassium Hydrogen phthalate solution and a 2-4 g/L sodium hydroxide solution, and R2 is a 3-5 g/L chloramine T solution;
   (4) pumping a sample to be detected from a sampling pipe to the stripping tube through the peristaltic pump;
   (5) adding a chemical agent R4 to the stripping tube for catalytic elimination; wherein R4 is a mixed solution of a 3-5 g/L sodium hydroxide solution with a concentration of and a 18-22 g/L citric acid solution;
   (6) pumping the sample to be detected in the stripping tube by an air pump to a UV digester and then to the heater; instantaneously vaporizing the sample to be detected by distillation in the heater to release a cyanide gas; cooling the cyanide gas into a cyanide liquid by a condenser; allowing the cyanide liquid to flow into the mixing tube to react with the mixed chemical agent solution obtained in step (3); and repeating the distillation until the sample to be detected is completely vaporized;
   (7) adding a chemical agent R3 to the mixing tube for color development, wherein R3 is a mixed solution of pyridine with a volume fraction of 99% or more, barbituric acid with a mass concentration of 28-32 g/L and concentrated hydrochloric acid; subjecting the reaction mixture to standing for a certain period after the color development; measuring a final absorbance of the reaction mixture; and calculating the total cyanide content in the sample to be detected according to spectrophotometry; and
   (8) pumping pure water to empty and clean the mixing tube, the stripping tube, the UV digester, the heater and the condenser.

8. The method of claim 7, wherein the sample to be detected in step (4) is a water sample to be monitored or a standard sample; the water sample to be monitored is collected to the sampling pipe through a water sample-monitoring tube, and then pumped into the stripping tube through the peristaltic pump; and the standard sample is collected to the sampling pipe through a standard sample tube, and then pumped into the stripping tube through the peristaltic pump.

9. The method of claim 7, wherein in step (3), air is pumped into the mixing tube to completely mix the chemical agents R3 and R4 with pure water; and in step (4), the excess sample to be detected in the stripping tube is discharged from a drain pipe which is provided at an upper portion of the stripping tube.

10. The method of claim 7, wherein in step (1), the heater has an internal temperature of 80° C., a pulse-heating temperature of 162° C. and a maximum temperature of 165° C.

\* \* \* \* \*